United States Patent
Mohapatra

(10) Patent No.: US 9,696,904 B1
(45) Date of Patent: Jul. 4, 2017

(54) FACILITATING TEXT ENTRY FOR MOBILE HEALTHCARE APPLICATION

(71) Applicant: ALLSCRIPTS SOFTWARE, LLC, Chicago, IL (US)

(72) Inventor: Sweta Mohapatra, Raleigh, NC (US)

(73) Assignee: ALLSCRIPTS SOFTWARE, LLC, Chicago, IL (US)

( * ) Notice: Subject to any disclaimer, the term of this patent is extended or adjusted under 35 U.S.C. 154(b) by 310 days.

(21) Appl. No.: 14/528,865

(22) Filed: Oct. 30, 2014

(51) Int. Cl.
G06F 3/0488 (2013.01)

(52) U.S. Cl.
CPC .............. G06F 3/04886 (2013.01)

(58) Field of Classification Search
CPC ................................. G06F 3/04886
See application file for complete search history.

(56) References Cited

U.S. PATENT DOCUMENTS

| | | | | |
|---|---|---|---|---|
| 5,845,300 A * | 12/1998 | Comer | ............... | G06F 17/276 715/203 |
| 6,208,339 B1 * | 3/2001 | Atlas | ............... | G06F 3/0481 715/205 |
| 6,377,965 B1 * | 4/2002 | Hachamovitch | ...... | G06T 19/00 715/205 |
| 6,564,213 B1 * | 5/2003 | Ortega | ............... | G06F 17/3064 |
| 7,181,497 B1 * | 2/2007 | Appelman | ............ | G06Q 10/107 709/206 |
| 7,216,292 B1 * | 5/2007 | Snapper | ............... | G06F 17/243 715/234 |
| 7,343,551 B1 * | 3/2008 | Bourdev | ............... | G06F 17/243 715/224 |
| 7,539,472 B2 * | 5/2009 | Sloo | ............... | G06F 9/4443 345/169 |
| 8,230,336 B2 * | 7/2012 | Morrill | ............... | G06F 17/2235 715/205 |
| 8,234,561 B1 * | 7/2012 | Bourdev | ............... | G06F 17/243 715/224 |
| 8,347,222 B2 * | 1/2013 | Raguseo | ............... | G06F 3/0237 715/780 |
| 8,645,825 B1 * | 2/2014 | Cornea | ............... | G06F 17/276 715/257 |
| 8,843,845 B2 * | 9/2014 | Ouyang | ............... | G06F 3/04883 715/773 |
| 8,850,310 B2 * | 9/2014 | Rampson | ............... | G06F 3/0237 715/234 |

(Continued)

Primary Examiner — Jung-Mu Chuang
(74) Attorney, Agent, or Firm — Tillman Wright, PLLC; Chad D. Tillman; Jeremy C. Doerre

(57) ABSTRACT

A method for facilitating entry of items for a healthcare software application loaded on an electronic device includes displaying, to a healthcare practitioner via a display of a mobile electronic device, an interface of a healthcare software application including a text entry box and a virtual keyboard; receiving, from the healthcare practitioner via the virtual keyboard, first input corresponding to entry of a first text string; continuously, during entry of the first text string, comparing input characters to a maintained list of items associated with healthcare, and displaying a popover including items found to match, based on the comparing, input characters; receiving, from the healthcare practitioner, second input corresponding to selection of a particular item displayed in the popover; and inserting, into the text entry box based on the received second input, a text string corresponding to the selected particular item.

18 Claims, 4 Drawing Sheets

(56) References Cited

U.S. PATENT DOCUMENTS

| | | | | |
|---|---|---|---|---|
| 8,947,355 B1* | 2/2015 | Karakotsios | G06F 3/017 | 345/156 |
| 9,104,312 B2* | 8/2015 | Kay | G06F 3/04883 | |
| 9,230,238 B2* | 1/2016 | Zappa | G06Q 10/10 | |
| 9,292,537 B1* | 3/2016 | Lee | G06F 17/3012 | |
| 9,355,090 B2* | 5/2016 | Goldsmith | G06F 3/018 | |
| 9,454,677 B1* | 9/2016 | Sinclair | F01P 7/16 | |
| 9,471,581 B1* | 10/2016 | Lee | G06F 3/0482 | |
| 9,477,653 B2* | 10/2016 | McKenzie | G06F 3/0482 | |
| 2002/0138292 A1* | 9/2002 | Tang | G06F 17/3064 | 715/730 |
| 2004/0153338 A1* | 8/2004 | Kim | G06F 19/322 | 705/2 |
| 2005/0022114 A1* | 1/2005 | Shanahan | G06F 21/10 | 715/234 |
| 2005/0108344 A1* | 5/2005 | Tafoya | G06Q 10/107 | 709/206 |
| 2005/0131738 A1* | 6/2005 | Morris | G06F 19/322 | 705/2 |
| 2006/0142997 A1* | 6/2006 | Jakobsen | G06F 3/0237 | 704/10 |
| 2006/0173683 A1* | 8/2006 | Roth | G10L 15/183 | 704/251 |
| 2007/0060176 A1* | 3/2007 | Sloo | G06F 9/4443 | 455/466 |
| 2007/0296615 A1* | 12/2007 | Raguseo | G06F 3/0237 | 341/51 |
| 2008/0065617 A1* | 3/2008 | Burke | G06F 17/30646 | |
| 2008/0294982 A1* | 11/2008 | Leung | G06F 17/276 | 715/261 |
| 2010/0275109 A1* | 10/2010 | Morrill | G06F 17/2235 | 715/205 |
| 2012/0197660 A1* | 8/2012 | Prodanovich | G06Q 30/04 | 705/2 |
| 2013/0073306 A1* | 3/2013 | Shlain | G06Q 10/06 | 705/2 |
| 2013/0096938 A1* | 4/2013 | Stueckemann | G06F 19/34 | 705/2 |
| 2014/0104177 A1* | 4/2014 | Ouyang | G06F 3/04883 | 345/168 |
| 2014/0180711 A1* | 6/2014 | Kamen | G06Q 10/06 | 705/2 |
| 2014/0365874 A1* | 12/2014 | Rampson | G06F 3/0482 | 715/243 |
| 2014/0379361 A1* | 12/2014 | Mahadkar | G06F 19/328 | 705/2 |
| 2015/0025904 A1* | 1/2015 | Rao | G06Q 50/22 | 705/2 |
| 2016/0099904 A1* | 4/2016 | Agathangelos | H04L 51/28 | 709/206 |

\* cited by examiner

FACILITATING TEXT ENTRY FOR MOBILE HEALTHCARE APPLICATION

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE INVENTION

The present invention generally relates to facilitating text entry for healthcare software applications.

Frequently, when using software for mobile devices, a user can either enter free text into a data entry field, or choose an item from a list. In cases where both list selection and free text are available, a user is typically forced to switch between the two in order to complete a task.

A need exists for improvement in software for mobile devices. This need and other needs are addressed by one or more aspects of the present invention.

SUMMARY OF THE INVENTION

The present invention includes many aspects and features. Moreover, while many aspects and features relate to, and are described in particular context, the present invention is not limited to use only in this context, as will become apparent from the following summaries and detailed descriptions of aspects, features, and one or more embodiments of the present invention.

Accordingly, one aspect of the present invention relates to a method for facilitating entry of items for a healthcare software application loaded on an electronic device, the method comprising displaying, to a healthcare practitioner via a display of a mobile electronic device, an interface of a healthcare software application including a text entry box and a virtual keyboard; receiving, from the healthcare practitioner via the virtual keyboard, first input corresponding to entry of a first text string; continuously, during entry of the first text string, comparing input characters to a maintained list of items associated with healthcare, and displaying a popover including items found to match, based on the comparing, input characters; receiving, from the healthcare practitioner, second input corresponding to selection of a particular item displayed in the popover; and inserting, into the text entry box based on the received second input, a text string corresponding to the selected particular item.

In a feature of this aspect, the mobile electronic device comprises a phone.

In a feature of this aspect, the mobile electronic device comprises a tablet.

In a feature of this aspect, the display comprises a touchscreen.

In a feature of this aspect, the healthcare practitioner comprises a nurse.

In a feature of this aspect, the healthcare practitioner comprises a doctor.

In a feature of this aspect, the maintained list of items is maintained at the mobile electronic device.

In a feature of this aspect, the maintained list of items is maintained at a remote server.

In a feature of this aspect, the maintained list of items is maintained in a database.

Another aspect relates to a method for facilitating entry of items for a healthcare software application loaded on an electronic device, the method comprising displaying, to a healthcare practitioner via a display of a mobile electronic device, an interface of a healthcare software application including a text entry box and a virtual keyboard; receiving, from the healthcare practitioner via the virtual keyboard, first input corresponding to entry of a first text string; continuously, during entry of the first text string, comparing input characters to a maintained list of items associated with healthcare, and displaying a popover including items found to match, based on the comparing, input characters; receiving, from the healthcare practitioner, second input corresponding to selection of a particular item displayed in the popover; inserting, into the text entry box based on the received second input, a text string corresponding to the selected particular item; and updating, based on the received second input, a favorites list of previously selected items.

Another aspect relates to a method for facilitating entry of items for a healthcare software application loaded on an electronic device, the method comprising displaying, to a healthcare practitioner via a display of a mobile electronic device, an interface of a healthcare software application including a text entry box and a virtual keyboard; receiving, from the healthcare practitioner via the virtual keyboard, first input corresponding to entry of a first text string; continuously, during entry of the first text string, comparing input characters to a maintained list of items associated with healthcare, and displaying a popover including items found to match, based on the comparing, input characters; receiving, from the healthcare practitioner, second input corresponding to selection of a particular item displayed in the popover; inserting, into the text entry box based on the received second input, a text string corresponding to the selected particular item; updating, based on the received second input, a favorites list of previously selected items; displaying, to the healthcare practitioner via the display of the mobile electronic device, an interface of a healthcare software application including a second text entry box and a virtual keyboard; receiving, from the healthcare practitioner via the virtual keyboard, third input corresponding to entry of a second text string; continuously, during entry of the second text string, comparing input characters to a maintained list of items associated with healthcare, and displaying a second popover including items found to match, based on the comparing, input characters, the second popover including one or more items in the favorites list displayed at a top of the second popover; receiving, from the healthcare practitioner, fourth input corresponding to selection of a second particular item displayed in the second popover; inserting, into the second text entry box based on the received fourth input, a text string corresponding to the selected second particular item; and updating, based on the received fourth input, the favorites list.

In addition to the aforementioned aspects and features of the present invention, it should be noted that the present invention further encompasses the various possible combinations and subcombinations of such aspects and features. Thus, for example, any aspect may be combined with an aforementioned feature in accordance with the present invention without requiring any other aspect or feature.

BRIEF DESCRIPTION OF THE DRAWINGS

One or more preferred embodiments of the present invention now will be described in detail with reference to the accompanying drawings, wherein the same elements are referred to with the same reference numerals, and wherein, FIGS. 1-2 illustrate an exemplary interface of a healthcare software application loaded on a tablet;

FIG. 3 illustrates display of an item on a favorites list ahead of other items in a popover.

DETAILED DESCRIPTION

Figure 4:
FIG. 4 illustrates entry of text into a text box following selection of an item from a popover.

As a preliminary matter, it will readily be understood by one having ordinary skill in the relevant art ("Ordinary Artisan") that the present invention has broad utility and application. As should be understood, any embodiment may incorporate only one or a plurality of the above-disclosed aspects of the invention and may further incorporate only one or a plurality of the above-disclosed features. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention in any claim of a patent issuing here from, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the issued claim(s) rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. §112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, one or more preferred embodiments of the present invention are next described. The following description of one or more preferred embodiments is merely exemplary in nature and is in no way intended to limit the invention, its implementations, or uses.

In accordance with one or more preferred implementations, a healthcare software application loaded on a mobile device is configured to allow a user to input free text into a text box and provide a pop up including items in a list partly matching an input string.

Figure 1:
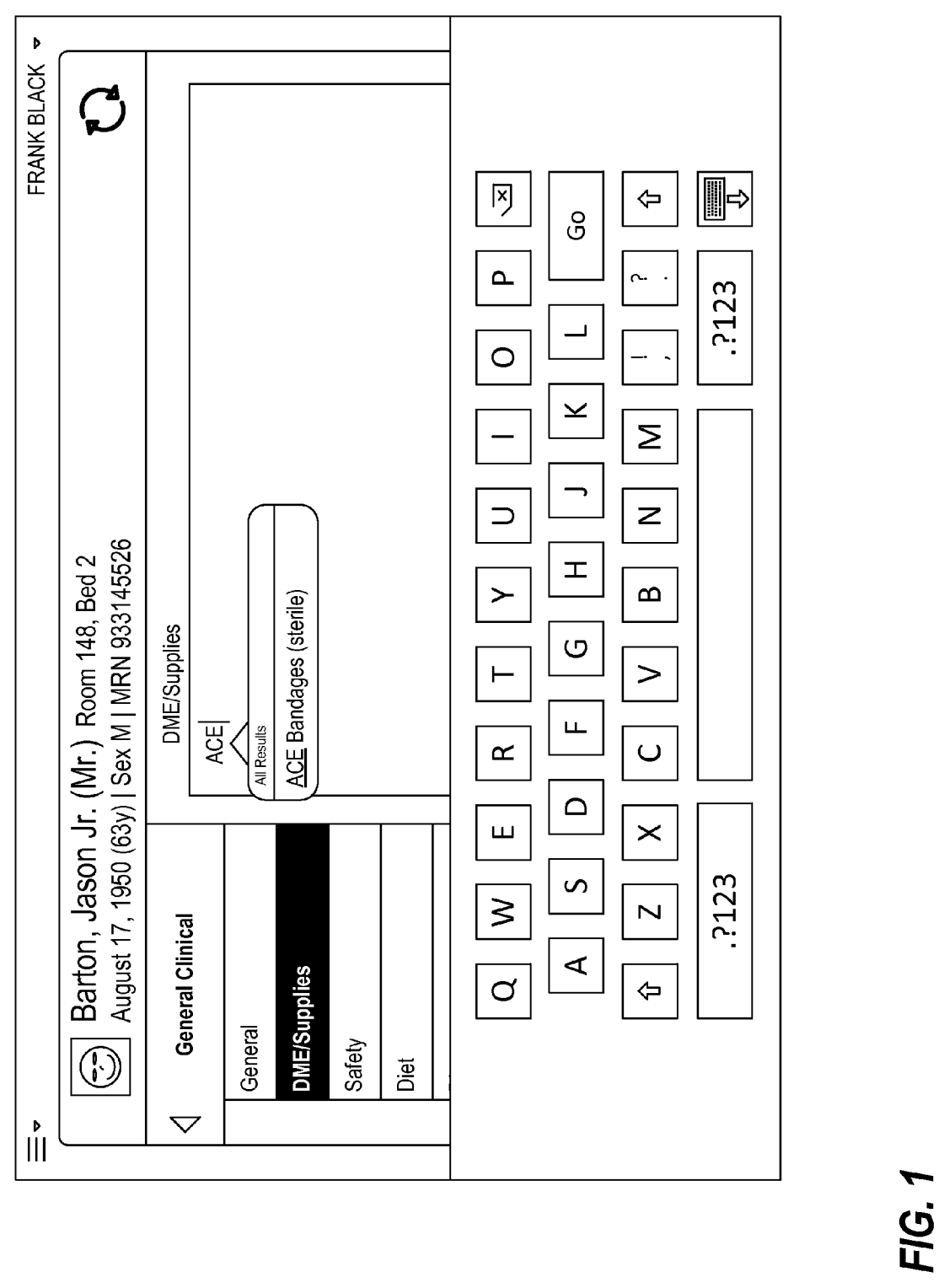
Figure 2:
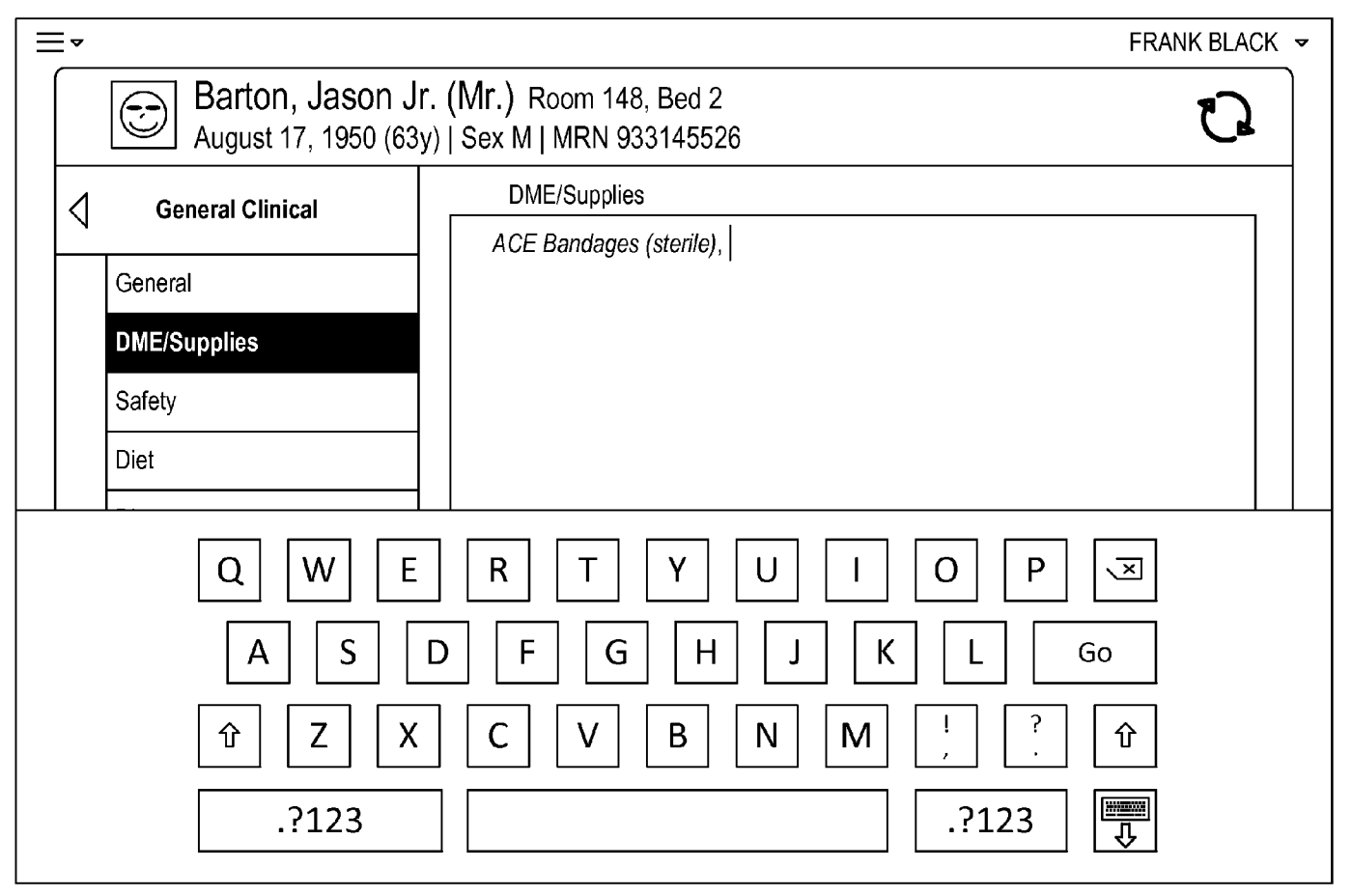

For example, FIG. 1 illustrates an exemplary interface of a healthcare software application loaded on a tablet where a user has input the string "ACE" into a text box and the software pops up a potential matching result of "ACE Bandages (sterile)" for potential selection by the user to speed up entry of that item. Preferably, the user can simply touch the "ACE Bandages (sterile)" result to have the result completed in the text box, as illustrated in FIG. 2. In one or more preferred implementations, the system further inserts a divider (such as a comma) and a space following the item, allowing the user to begin entering a next item in the list.

In one or more preferred implementations, when a user begins to enter text, the text string input is continuously compared against a maintained list of strings to determine whether any of the maintained strings match the input string. The matching strings are preferably displayed in a popover, as illustrated in FIG. 1. In one or more preferred implementations, a list of strings is stored remotely at a server or database (although in at least some implementations a list may be stored locally) and retrieved for comparison. Such comparison may occur locally at a mobile electronic device, or remotely at a server.

In one or more preferred implementations, an item added via autofill from a popover is displayed in a different color or in italics, as illustrated in FIG. 2. Preferably, a user can tap on an item added via a popover and a popover will be displayed showing other items that are similar to the selected item.

In one or more preferred implementations, such a popover will further allow a user to delete the item inserted via a popover. Additionally or alternatively, in one or more preferred implementations, a user can delete an autofilled item using a backspace button (e.g. on a virtual keyboard). Preferably, text will change from blue or italics back to normal when a letter is deleted.

Figure 3:
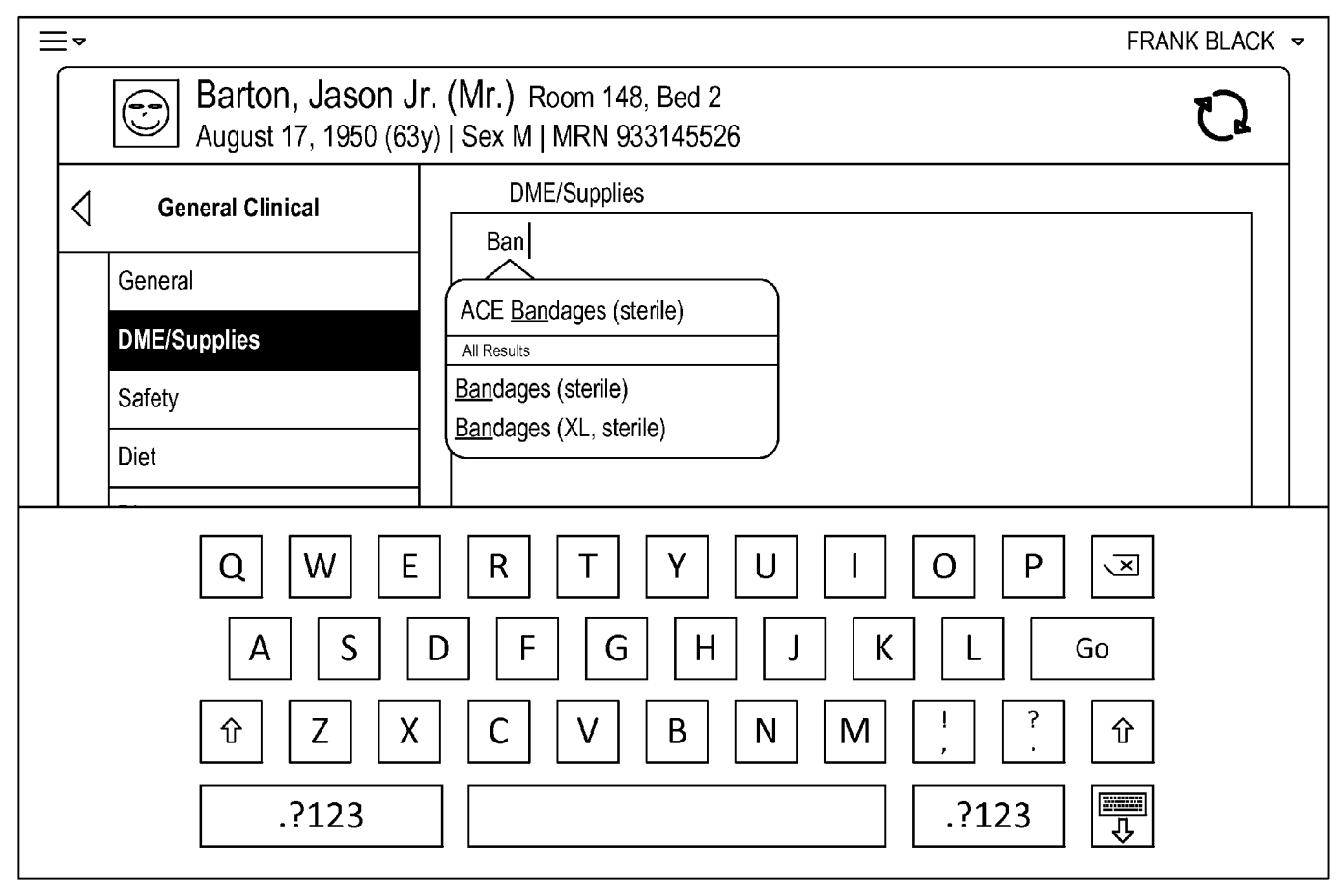

In one or more preferred implementations, if a user selects an item via a popover, that item is subsequently stored in a short list or favorites list. This favorites list can be updated as items are selected. Such a favorites list is preferably dynamically updated based on how many times a user has chosen a particular item. In one or more preferred implementations, items from such a favorites list are shown before results from an entire list, as illustrated in FIG. 3, where "ACE Bandages (sterile)" is shown ahead of other items on the list because it was previously selected by the user.

After selecting an item from the popover, the user can continue typing and can manually enter items that do not match a stored list, as illustrated in FIG. 4.

In one or more preferred implementations, a user can specify a list of items to be accessed during text entry.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention. Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

What is claimed is:

1. A method for facilitating entry of items for a healthcare software application loaded on an electronic device, the method comprising:
    (a) displaying, to a healthcare practitioner via a display of a mobile electronic device, an interface of a healthcare software application including a text entry box and a virtual keyboard;
    (b) receiving, from the healthcare practitioner via the virtual keyboard, a first input corresponding to an entry of a first text string;
    (c) continuously, during the entry of the first text string,
        (i) comparing input characters of the first input to a maintained list of items associated with healthcare, and
        (ii) displaying a first popover including items found to match, based on the comparing, input characters of the first input;
    (d) receiving, from the healthcare practitioner, a second input corresponding to a selection of a first particular item displayed in the first popover;
    (e) based on the received second input,
        (i) replacing the first text string with a second text string corresponding to the selected first particular item, the second text string being color-coded with a specific color to indicate an input via an autofill from a popover,
        (ii) inserting a comma and space, and
        (iii) updating a favorites list of previously selected items to include the selected first particular item;
    (f) receiving, from the healthcare practitioner via the virtual keyboard, a third input corresponding to an entry of a third text string;
    (g) continuously, during the entry of the third text string,
        (i) comparing input characters of the third input to the maintained list of items associated with healthcare, including items on the favorites list of previously selected items, and
        (ii) displaying a second popover including items found to match, based on the comparing, input characters of the third input, the second popover including one or more items in the favorites list displayed at a top of the second popover;
    (h) receiving, from the healthcare practitioner, a fourth input corresponding to a selection of a second particular item displayed in the second popover;
    (i) based on the received fourth input,
        (i) replacing the third text string with a fourth text string corresponding to the selected second particular item, the fourth text string being color-coded with the specific color to indicate an input via an autofill from a popover,
        (ii) inserting a comma and space, and
        (iii) updating the favorites list of previously selected items to include the selected second particular item;
    (j) receiving, from the healthcare practitioner, a fifth input corresponding to a deletion of a character of the fourth text string;
    (k) changing, based on the fifth input corresponding to the deletion of the character of the fourth text string, a color of the fourth text string to no longer be the specific color;
    (l) receiving, from the healthcare practitioner, a sixth input corresponding to a tapping engagement with the color-coded second text string;
    (m) in response to the received sixth input corresponding to the tapping engagement with the color-coded second text string, highlighting the color-coded second text string and displaying a third popover including items similar to the highlighted second text string;
    (n) receiving, from the healthcare practitioner, a seventh input corresponding to an engagement with the third popover, such engagement comprising a selection of a third particular item displayed in the third popover; and
    (o) in response to the seventh input corresponding to the engagement with the third popover, deleting the highlighted second text string and inserting a fifth text string corresponding to the third particular item.

2. The method of claim 1, wherein the mobile electronic device comprises a phone.

3. The method of claim 1, wherein the mobile electronic device comprises a tablet.

4. The method of claim 1, wherein the display comprises a touchscreen.

5. The method of claim 1, wherein the healthcare practitioner comprises a nurse.

6. The method of claim 1, wherein the healthcare practitioner comprises a doctor.

7. The method of claim 1, wherein the maintained list of items is maintained at the mobile electronic device.

8. The method of claim 1, wherein the maintained list of items is maintained at a remote server.

9. The method of claim 1, wherein the maintained list of items is maintained in a database.

10. A method for facilitating entry of items for a healthcare software application loaded on an electronic device, the method comprising:
   (a) displaying, to a healthcare practitioner via a display of a mobile electronic device, an interface of a healthcare software application including a text entry box and a virtual keyboard;
   (b) receiving, from the healthcare practitioner via the virtual keyboard, a first input corresponding to an entry of a first text string;
   (c) continuously, during the entry of the first text string,
      (i) comparing input characters of the first input to a maintained list of items associated with healthcare, and
      (ii) displaying a first popover including items found to match, based on the comparing, input characters of the first input;
   (d) receiving, from the healthcare practitioner, a second input corresponding to a selection of a first particular item displayed in the first popover;
   (e) based on the received second input,
      (i) replacing the first text string with a second text string corresponding to the selected first particular item, the second text string being italicized to indicate an input via an autofill from a popover,
      (ii) inserting a comma and space, and
      (iii) updating a favorites list of previously selected items to include the selected first particular item;
   (f) receiving, from the healthcare practitioner via the virtual keyboard, a third input corresponding to an entry of a third text string;
   (g) continuously, during the entry of the third text string,
      (i) comparing input characters of the third input to the maintained list of items associated with healthcare, including items on the favorites list of previously selected items, and
      (ii) displaying a second popover including items found to match, based on the comparing, input characters of the third input, the second popover including one or more items in the favorites list displayed at a top of the second popover;
   (h) receiving, from the healthcare practitioner, a fourth input corresponding to a selection of a second particular item displayed in the second popover;
   (i) based on the received fourth input,
      (i) replacing the third text string with a fourth text string corresponding to the selected second particular item, the fourth text string being italicized to indicate an input via an autofill from a popover,
      (ii) inserting a comma and space, and
      (iii) updating the favorites list of previously selected items to include the selected second particular item;
   (j) receiving, from the healthcare practitioner, a fifth input corresponding to a deletion of a character of the fourth text string;
   (k) changing, based on the fifth input corresponding to the deletion of the character of the fourth text string, the fourth text string to no longer be italicized;
   (l) receiving, from the healthcare practitioner, a sixth input corresponding to a tapping engagement with the italicized second text string;
   (m) in response to the received sixth input corresponding to the tapping engagement with the italicized second text string, highlighting the italicized second text string and displaying a third popover including items similar to the highlighted second text string;
   (n) receiving, from the healthcare practitioner, a seventh input corresponding to an engagement with the third popover, such engagement comprising a selection of a third particular item displayed in the third popover; and
   (o) in response to the seventh input corresponding to the engagement with the third popover, deleting the highlighted second text string and inserting a fifth text string corresponding to the third particular item.

11. The method of claim 10, wherein the mobile electronic device comprises a phone.

12. The method of claim 10, wherein the mobile electronic device comprises a tablet.

13. The method of claim 10, wherein the display comprises a touchscreen.

14. The method of claim 10, wherein the healthcare practitioner comprises a nurse.

15. The method of claim 10, wherein the healthcare practitioner comprises a doctor.

16. The method of claim 10, wherein the maintained list of items is maintained at the mobile electronic device.

17. The method of claim 10, wherein the maintained list of items is maintained at a remote server.

18. The method of claim 10, wherein the maintained list of items is maintained in a database.

* * * * *